United States Patent [19]

Wedemeyer et al.

[11] 4,060,562
[45] Nov. 29, 1977

[54] PROCESS FOR PREPARING META-SUBSTITUTED HALOPHENOLS

[75] Inventors: Karlfried Wedemeyer, Cologne; Wolfgang Kiel, Schildgen; Werner Evertz, Monheim, all of Germany

[73] Assignee: Bayer Aktiengesellschaft, Leverkusen, Germany

[21] Appl. No.: 609,140

[22] Filed: Aug. 29, 1975

[30] Foreign Application Priority Data

Sept. 10, 1974 Germany .............................. 2443152

[51] Int. Cl.² .............................................. C07C 39/30
[52] U.S. Cl. ................................................ 260/623 R
[58] Field of Search ........... 260/623 R, 619 R, 619 A, 260/620

[56] References Cited

U.S. PATENT DOCUMENTS

| | | | |
|---|---|---|---|
| 3,912,782 | 10/1975 | Wolfgang et al. | 260/623 R |
| 3,912,783 | 10/1975 | Wedemeyer et al. | 260/623 R |

*Primary Examiner*—James O. Thomas, Jr.
*Assistant Examiner*—W. B. Lone
*Attorney, Agent, or Firm*—Burgess, Dinklage & Sprung

[57] ABSTRACT

Phenols, meta-substituted by halogen are prepared by reacting halogenophenols of the formula

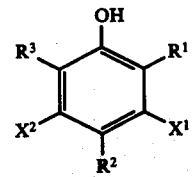

wherein
$X^1$ and $X^2$ are identical or different and represent halogen, hydrogen or optionally substituted aryl or aralkyl, with at least one of the radicals $X^1$ or $X^2$ representing halogen, and
$R^1$, $R^2$ and $R^3$ are identical or different and represent hydrogen or optionally monosubstituted or polysubstituted aryl or aralkyl or chlorine, bromine or iodine, with at least one of the radicals $R^1$, $R^2$ and $R^3$ representing chlorine, bromine or iodine, with hydrogen under pressure at elevated temperature in the presence of elemental sulfur, or compounds thereof optionally in the presence of active charcoal and/or iron salts.

11 Claims, No Drawings

PROCESS FOR PREPARING META-SUBSTITUTED HALOPHENOLS

BACKGROUND

The invention relates to a process for the preparation of meta-substituted halogenophenols by selective dehalogenation of more highly halogenated phenols.

The 3-halogenophenols and 3,5-dihalogenophenols obtainable in accordance with the process of the invention can only be synthesised in a highly labor-intensive and cost-intensive manner if the processes of preparation hitherto known are used. For example, the preparation of 3,5-dichlorophenol hitherto customary is carried out via the chlorination of p-nitroaniline to 1-amino-2,6-dichloro-4-nitrobenzene. The amino group is then diazotized and replaced by hydrogen, by reduction. The resulting 3,5-dichloro-nitrobenzene is in turn reduced to 3,5-dichloroaniline, which is then diazotized, and the product is boiled to give 3,5-dichlorophenol (Journal of the Chemical Society, London, 1927, 2217; Ber. dtsch. chem. Ges. 8, 143; Japanese Patent Application No. 4,862,729-Q). Processes which start from the halogenation of a nitrobenzene require catalytic reduction of the 3-halogeno-1-nitrobenzene, thus obtained, to the corresponding aniline, and subsequent diazotisation and boiling to give the 3-halogenophenol (compare Beilsteins Handbook of Organic Chemistry, 4th edition, volume VI, page 185).

The catalyst hydrogenation of halogenated phenols is also known. However, the hydrogenation does not take place selectively and leads either exclusively to phenols or to mixtures of different chlorophenols (Houben-Weyl, Methods of Organic Chemistry, 4th edition, volume V/IV, page 772). Thus, for example, the hydrogenation of pentachlorophenol with Raney nickel as the catalyst leads to complete dehalogenation (Bull. Soc. Chim. Fr. 1963, 2442) and the hydrogenation of polychlorophenols in the gas phase, over an activated alumina catalyst which has been treated with copper-(I) chloride, leads to mixtures of phenols of various chlorine contents (German Published Specification Mo. 1,109,701).

SUMMARY

The present invention provides a process for the preparation of a phenol which is meta-substituted by halogen, which comprises reacting a halogenophenol of the general formula I

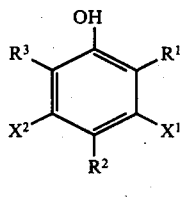

wherein
$X^1$ and $X^2$ are identical or different and represent halogen, hydrogen, or an optionally substituted aryl or aralkyl radical, at least one of the radicals $X^1$ or $X^2$ representing halogen, and
$R^1$, $R^2$ and $R^3$ are identical or different and represent hydrogen or an optionally monosubstituted or polysubstituted aryl or aralkyl radical or chlorine, bromine or iodine, at least one of the radicals $R^1$, $R^2$ and $R^3$ representing chlorine, bromine or iodine, with hydrogen under pressure at elevated temperature in the presence of sulphur, in the form of the element or of a compound, if appropriate in the presence of active charcoal and/or an iron salt.

Correspondingly, the process according to the invention produces halogenophenols which are meta-substituted by halogen and have the general formula II

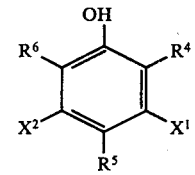

wherein
$X^1$ and $X^2$ have the same range of meanings as in the general formula I and
$R^4$, $R^5$ and $R^6$ are identical or different and represent hydrogen or an optionally monosubstituted or polysubstituted aryl radical or an aralkyl radical or, in the case that the radical $R^1$, $R^2$ or $R^3$ in the formula I represents chlorine, bromine or iodine, each represent hydrogen.

As substituents $X^1$ and $X^2$ on the phenyl nucleus, halogen atoms to be mentioned are fluorine, chlorine, bromine or iodine, preferably chlorine or fluorine, and particularly preferentially chlorine.

DESCRIPTION

Examples of aryl radicals to be mentioned are the benzene or naphthalene radical, and aralkyl radicals to be mentioned are those with 7 to 18 carbon atoms of which the alkyl portion contains up to 6 carbon atoms and is preferably straight-chain and saturated, and of which the aromatic portion is the benzene or naphthalene radical. Examples of substituents of the aryl and aralkyl radicals which may be mentioned are straight-chain or branched, preferably saturated, alkyl radicals with 1 to 6 carbon atoms, cycloalkane radicals with 5 to 6 carbon atoms in the ring, fluorine, chlorine, bromine or iodine, or the hydroxyl groups. Unsubstituted and monosubstituted aryl or aralkyl radicals are preferred. Examples of radicals which may be mentioned are phenyl, naphthyl, o-tolyl, m-tolyl, p-tolyl, p-ethylphenyl, m-ethylphenyl, p-ethylphenyl, o-tert.-butyl-phenyl, m-tert.-butylphenyl, p-tert.-butyl-phenyl, o-hexyl-phenyl, m-hexyl-phenyl, p-hexyl-phenyl, o-fluoro-phenyl, m-fluoro-phenyl, p-fluoro-phenyl, o-chloro-phenyl, m-chloro-phenyl, p-chloro-phenyl, o-bromo-phenyl, m-bromo-phenyl, p-bromo-phenyl, o-iodo-phenyl, m-iodo-phenyl, p-iodo-phenyl, o-hydroxy-phenyl, m-hydroxy-phenyl, p-hydroxy-phenyl, 2-fluoro-naphthyl, 2-chloro-naphthyl, 2-bromo-naphthyl, 2-iodo-naphthyl, 2-hydroxy-naphthyl, 2-methyl-naphthyl, 2-ethyl-naphthyl, 2-iso-propyl-naphthyl, benzyl, 1-phenyl-ethyl, 1-phenyl-propyl, 2-phenyl-propyl, 1-phenyl-butyl, 1-phenyl-iso-butyl, 1-naphthyl-methyl and 1-naphthyl-iso-butyl.

Particularly preferred starting compounds are compounds of the general formula I, wherein
$X^1$ and $X^2$ are identical or different and represent fluorine, chlorine or hydrogen, with at least one of the radicals $X^1$ or $X^2$ representing fluorine or chlorine, and
$R^1$, $R^2$ and $R^3$ are identical or different and represent hydrogen, the phenyl radical, the benzyl radical or chlorine, with at least one of the radicals $R^1$, $R^2$ or $R^3$ representing chlorine.

The following may be mentioned as examples of preferentially used starting compounds: 2,3-, 2,5- and 3,4-dichlorophenol; 2,3,4-, 2,3,6-, 2,4,5-, 2,3,5- and 3,4,5-trichlorophenol; 2,3,4,6-, 2,3,4,5- and 2,3,5,6-tetrachlorophenol; pentachlorophenyl; 2-chloro-3-fluorophenol; 2-chloro-5-fluorophenol; 4-chloro-3-fluorophenol; 2,4-dichloro-3-fluorophenol; 2,6-dichloro-3-fluorophenol; 2,4-dichloro-5-fluorophenol; 2,3-dichloro-5-fluorophenol; 2-chloro-3,5-difluorophenol; 3,4-dichloro-5-fluorophenol; 3,5-difluoro-4-chlorophenol; 2,4,6-trichloro-3-fluorophenol; 2,4-dichloro-3,5-difluorophenol; 2,3,6-trichloro-5-fluorophenol; 2,6-dichloro-3,5-difluorophenol; 2,4,6-trichloro-3,5-difluorophenol; 2,3,4,6-tetrachloro-5-fluorophenol; 2,5-dichloro-6-benzylphenol; 2,5-dichloro-4-benzylphenol; 2,4,5-trichloro-6-benzylphenol; 2,3,4,5-tetrachloro-4-benzylphenol; 2,4-dichloro-5-fluoro-6-benzylphenol; 2,5-dichloro-4-phenylphenol; 2,3,6-trichloro-4-phenylphenol; 3,4,6-trichloro-2-phenylphenol; 2,3,5,6-tetrachloro-4-phenylphenol.

Correspondingly, the following may be mentioned as examples of compounds which are formed by the process according to the invention: 3-chlorophenol; 3,5-dichlorophenol; 3-fluorophenol; 3-chloro-5-fluorophenol; 3,5-difluorophenol; 2-benzyl-3-chlorophenol; 3-chloro-4-benzylphenol; 2-benzyl-3-fluorophenol; 3,5-dichloro-4-benzylphenol; 3-chloro-4-phenylphenol; 3-chloro-2-phenylphenol; 3,5-dichloro-4-phenylphenol.

Very particularly preferred starting compounds are compounds of the general formula I wherein $X^1$ and $X^2$ are identical or different and represent chlorine or hydrogen, with at least one of the radicals $X^1$ and $X^2$ representing chlorine and $R^1$, $R^2$ and $R^3$ are identical or different and represent hydrogen or chlorine, with at least one of the radicals $R^1$, $R^2$ or $R^3$ representing chlorine. The halogenophenols which can be employed in accordance with the process of the invention are known and are accessible by simple halogenation of the corresponding phenols or by saponification of polychlorobenzenes (U.S. Pat. Nos. 2,803,670, 2,755,307 and 2,708,209, and French Pat. No. 1,094,912).

The process according to the invention is carried out in the presence of sulphur which can be in the form of the element or of a compound. The sulphur compounds can be either inorganic or organic. Mixtures of sulphur compounds may be used, or mixtures of elementary sulphur with one or more sulphur compounds.

Examples of inorganic sulphur compounds which may be mentioned are hydrogen sulphide, and the sulphides or polysulphides of the alkali metals and alkaline earth metals, such as sodium sulphide and calcium sulphide, elementary sulphur or hydrogen sulphide being preferred.

Examples of organic sulphur compounds which may be mentioned are thiocarbonic acid derivatives, such as carbon disulphide, carbon oxysulphide, thiocarbonic acid ethyl ester, xanthic acid derivatives, such as sodium xanthate, thiourethanes, such as ethyl-thiourethane, thiourea, thiocarbonic acids and their derivatives, such as thioacetic acid, thiobenzoic acid, thioformamide, thioketones and thioaldehydes, such as thiobenzophenone and thioformaldehyde, thiols, such as methylmercaptan, benzylmercaptan, ethanedithiol and monothioglycol, thiophenols, thioalkanes such as diethyl sulphide, thiodiglycol, thioxane, dithiane and disulphides, such as diethyl disulphide and diphenyl disulphide, carbon disulphide or sodium xanthate being preferred. The amount of the sulphur or sulphur compounds used for the process according to the invention is in general about 0.1 to 20% by weight of sulphur, preferably about 0.5 to 15% by weight, and particularly preferentially 1 to 10% by weight, relative to the halogenophenol employed.

The sulphur or the compound containing sulphur may be added as a gas, liquid or solid. Of course, it is also possible to prepare solutions, emulsions or suspensions of the gaseous, liquid or solid sulphur compounds and meter these into the reaction medium.

In some cases it has proved advantageous to add catalytic amounts of iron salts to the reaction mixture. Examples of possible iron salts are iron-(II) sulphate, iron-(II) chloride, iron-(III) chloride or iron-(III) phosphate, preferably iron-(II) sulphate.

In general, the process according to the invention is carried out in the presence of a solvent which is inert under the reaction conditions; water and methanol may be mentioned as examples, water being preferred.

Since hydrogen halide is produced in the process according to the invention it has proved advantageous to add a hydrogen halide acceptor to the reaction mixture already before the reaction. The customary bases suitable as hydrogen halide acceptors can be used for this purpose. Tertiary amines, anilines and pyridine, as well as the hydroxides, carbonates, bicarbonates and acetates of the alkali metals, especially of sodium and potassium, and of the alkaline earth metals, especially calcium hydroxide, are used preferentially. The amount of the hydrogen halide acceptor employed is in general so chosen that at least one equivalent is employed for each halogen atom which is to be split off (that is to say halogen atoms which are not in the 3- or 5-position on the phenol nucleus).

The process according to the invention may be illustrated, by way of example, by the equation for the dehalogenation of pentachlorophenol to 3,5-dichlorophenol:

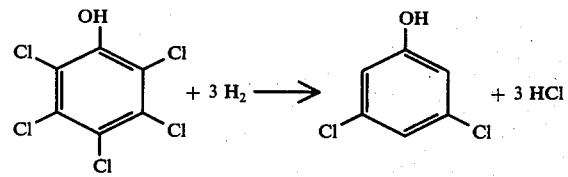

In general, the process is carried out by first introducing the starting material, solvent and hydrogen halide acceptor into an autoclave, adding the catalyst and, after sealing the autoclave, displacing the air with nitrogen and subsequently displacing the nitrogen with hydrogen.

To carry out the reaction, the hydrogen is passed as a gas into the reaction mixture. In general, the reaction is carried out at a hydrogen pressure of 20 to 250 atmospheres gauge, preferably of 40 to 220 atmospheres gauge and particularly preferentially of 50 to 200 atmospheres gauge.

The process according to the invention is in general carried out at a temperature of 100° to 350° C, preferably of 180° to 330° C, and particularly preferentially of 200° to 300° C.

After completion of the reaction, the 3-halogenophenol or 3,5-dihalogenophenol is brought into solution, or kept in solution, as the phenolate, by addition of alkali metal hydroxide; if necessary, solid catalyst constituents can be removed by filtration. The solution thus obtained is worked up in a manner which is in itself known, for example by acidification with a mineral acid, for example concentrated hydrochloric acid, extraction of the end product with an organic solvent, for example methylene chloride, and subsequent isolation from the organic phase, for example by fractional distillation.

The process according to the invention can be carried out discontinuously or continuously.

The surprising advantage of the process according to the invention is that it permits a simple selective dehalogenation of correspondingly more high halogenated phenols to the meta-substituted halogenophenols, according to the invention, by hydrogenation.

A further advantage of the process according to the invention is that phenol mixtures which are difficult to separate, and which in addition to the polyhalogenophenols, which are substituted by halogens in the m-position to the hydroxyl group, contain further halogenophenols or polyhalogenophenols in which there is no halogen is the m-position to the hydroxyl group, can also be used as the starting material. These latter compounds are dehalogenated by the process according to the invention to give phenol, which can easily be separated off by distillation. In contrast, the separation of the polyhalogenophenol mixture is involved and lengthy (compare German Published Specification No. 1,543,367).

The 3-halogenophenols and 3,5-dihalogenophenols obtainable by the process according to the invention are known intermediate products and can be used for the preparation of plant protection agents (German Pat. Nos. 921,970, 2,229,062, 1,116,656 and 814,152; U.S. Pat. Nos. 2,957,760, 3,346,397 and 3,080,225).

The following Examples illustrate the invention:

The examples were carried out in accordance with the general description of the experiment given below, using the starting materials and conditions described in Table 1.

The amounts of halogenophenol shown in Table 1, 250 ml of water and the sulphur or the sulphur compounds were introduced into an 0.7 l iron autoclave. Furthermore, for each halogen atom to be split off the equivalent amount of sodium hydroxide was added. The autoclave was closed and flushed with nitrogen before passing in the hydrogen. The hydrogenation of the reaction mixture was then carried out under the reaction conditions indicated in Table 1.

After completion of the reaction, the 3-halogenophenol or 3,5-dihalogenophenol was brought into solution as the phenolate by addition of sodium hydroxide and if necessary solid catalyst constituents were separated off by filtration. The reaction mixture was then brought to pH 1 with concentrated hydrochloric acid and the product is extracted with methylene chloride. After separating off the solvent, the residue was fractionally distilled.

Table 1
(Examples 1 – 11)

| Ex. No. | Halogenophenol amount employed | Sulfur compound amount employed | Content of halogenophenol in the reaction product | Yield % of theory | Reaction conditions: temperature, time, $H_2$ pressure |
|---|---|---|---|---|---|
| 1 | 2,5-Dichlorophenol 40.7 g | Carbon disulphide 6 g | 3-Chlorophenol 88.88% | 79 | 250°, 45 mins., 200 atms. gauge |
| 2 | 2,4,5-Trichlorophenol 49 g | Carbon disulphide 9 g | 3-Chlorophenol 81.28% | 67.5 | 200°, 60 mins., 200 atms. gauge |
| 3 | 2,4-Dichlorophenol 29.5 g | Thioxane 4.2 g | 3-Chlorophenol 67% | 39 | 300°, 45 mins., 200 atms. gauge |
| 4 | 2,4-Dichlorophenol 24.7 g | Thiodiglycol 3 g | 3-Chlorophenol 77.5% | 41 | 280°, 45 mins., 200 atms. gauge |
| 5 | 2,5-Dichlorophenol 40 g | Potassium xanthate 6 g | 3-Chlorophenol 96.97% | 69 | 250°, 45 mins. 200 atms. gauge |
| 6 | 2,5-Dichlorophenol 40 g | Sulphur 5 g | 3-Chlorophenol 90.48% | 70 | 250°, 45 mins., 200 atms. gauge |
| 7 | 2,5-Dichlorophenol 33.5 g | $Na_2S$ . 3 $H_2O$/carbon 6 g  5 g | 3-Chlorophenol 92.5% | 70 | 300°, 45 mins., 200 atms. gauge |
| 8 | 2,5-Dichlorophenol 40.7 g | Carbon disulphide 6 g | 3-Chlorophenol 75.1% | 50 | 250°, 45 mins., 200 atms. gauge/ using a tantalum autoclave |
| 9 | 2,5-Dichlorophenol 40.7 g | Carbon disulphide 6 g | 3-Chlorophenol 85.1% | 85.1 | 250°, 45 mins., 200 atms. gauge/using a tantalum autoclave and adding 6 g of $FeSO_4$ . $7H_2O$ |
| 10 | Pentachlorophenol 66 g | Carbon disulphide 7 g | 3,5-Dichlorophenol 86.11% | 44 | 230°, 30 mins., 200 atms. gauge |
| 11 | 4,4'-Dihydroxy-octachloro-diphenyl 50 g | Carbon disulphide 5 g | 4,4'-Dihydroxy-2,2'-6,6'-tetrachlorodiphenyl | 61.0 | 270°, 60 mins., 200 atms. gauge |

What is claimed is:

1. In a process for preparing a phenol which is meta-substituted by halogen by contacting a halogen phenol of the formula

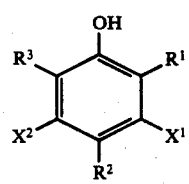

wherein $X^1$ and $X^2$ are identical or different and represent halogen, hydrogen, aryl selected from the group consisting of phenyl, naphthyl and aralkyl wherein the aralkyl group has 7 to 18 carbon atoms of which the alkyl portion has up to 6 carbon atoms, substituted aryl or substituted aralkyl wherein the substituent is selected from the group consisting of hydroxyl, halogen, alkyl having 1 to 6 carbon atoms, cycloalkyl having 5 to 6 carbon atoms, with at least one of the radicals $X^1$ or $X^2$ representing a halogen, and $R^1$, $R^2$ and $R^3$ are identical or different and represent hydrogen, aryl selected from the group consisting of phenyl, naphthyl and aralkyl having 7 to 18 carbon atoms of which the alkyl portion has up to 6 carbon atoms, substituted aryl or aralkyl wherein the substituent is a hydroxyl group, halogen, an alkyl group having 1 to 6 carbon atoms, a cycloalkyl group having 5 or 6 carbon atoms, chlorine, bromine or iodine, with at least one of the radicals $R^1$, $R^2$, and $R^3$ representing chlorine, bromine or iodine, with hydrogen under a pressure of 20 to 250 atmospheres at an elevated temperature of 100° to 350° C in the presence of a catalyst, the improvement which comprises employing as the catalyst a catalyst consisting essentially of elemental sulfur, an inorganic sulfur compound selected from the group consisting of hydrogen sulfide, a sulfide or polysulfide or an alkyali metal or alkaline earth metal, or an organic sulfur compound selected from the group consisting of carbon disulfide, carbon oxysulfide, thiocarbonic acid ethyl ester, a xanthic acid derivative, a thiourethane, thiourea, a thiocarbonic acid or its derivative, a thioaldehyde, a thiol, a thiophenol, a thioalkane, thioaxane, dithiane, disulfide and a thioketone.

2. Process of claim 1 wherein $X^1$ and $X^2$ are identical or different and represent fluorine, chlorine or hydrogen, with at least one of the radicals $X^1$ or $X^2$ representing fluorine or chlorine, and $R^1$, $R^2$ and $R^3$ are identical or different and represent hydrogen, phenyl, benzyl or chlorine, with at least one of the radicals $R^1$, $R^2$ or $R^3$ representing chlorine.

3. Process of claim 1 wherein $X^1$ and $X^2$ are identical or different and represent chlorine or hydrogen, with at least one of the radicals $X^1$ and $X^2$ representing chlorine and $R^1$, $R^2$ and $R^3$ are identical or different and represent hydrogen or chlorine, with at least one of the radicals $R^1$, $R^2$ or $R^3$ representing chlorine.

4. Process of claim 1 wherein the reaction is carried out in the presence of elemental sulfur.

5. Process of claim 1 wherein the reaction is carried out in the presence of inorganic sulfur compounds.

6. Process of claim 5 wherein the reaction is carried out in the presence of the sulfides of the alkali metals or alkaline earth metals.

7. Process of claim 5 wherein the reaction is carried out in the presence of the polysulfides of the alkali metals or alkaline earth metals.

8. Process of claim 1 wherein the reaction is carried out in the presence of organic sulfur compounds.

9. Process of claim 8 wherein the reaction is carried out in the presence of carbon disulfide.

10. Process of claim 8 wherein the reaction is carried out in the presence of derivatives of thiocarbonic acid or of xanthic acid.

11. A process according to claim 1 wherein the catalyst consists essentially of hydrogen sulfide, a sulfide or polysulfide of an alkali or alkaline earth metal, carbon disulfide, carbon oxysulfide, thiocarbonic acid ethyl ester, sodium xanthate, ethyl thiourethane, thiourea, thio acetic acid, thio benzoic acid, thioformamide, thiobenzophenone, thioformaldehyde, methylmercaptan, benzylmercaptan, ethanediol, monothioglycol, diethylsulfide, thiodiglycol, thiaxane, dithiane, diethyldisulfide and diphenyldisulfide.

* * * * *